(12) United States Patent
Kempe et al.

(10) Patent No.: US 8,207,510 B2
(45) Date of Patent: Jun. 26, 2012

(54) METHOD AND ARRANGEMENT FOR COLLIMATED MICROSCOPIC IMAGING

(75) Inventors: Michael Kempe, Jena (DE); Gerhard Krampert, Jena (DE); Matthias Wald, Kunitz (DE); Ralf Wolleschensky, Jena (DE)

(73) Assignee: Carl Zeiss Micro Imaging GmbH, Jena (DE)

( * ) Notice: Subject to any disclaimer, the term of this patent is extended or adjusted under 35 U.S.C. 154(b) by 0 days.

(21) Appl. No.: 13/042,137

(22) Filed: Mar. 7, 2011

(65) Prior Publication Data
US 2011/0215258 A1   Sep. 8, 2011

Related U.S. Application Data

(63) Continuation of application No. 12/444,290, filed as application No. PCT/EP2007/008556 on Oct. 2, 2007, now abandoned.

(30) Foreign Application Priority Data

Oct. 6, 2006   (DE) .......................... 10 2006 047 912

(51) Int. Cl.
*G01J 1/58* (2006.01)
(52) U.S. Cl. ................ 250/459.1; 250/458.1; 250/208.1
(58) Field of Classification Search .............. 250/458.1, 250/459.1; 356/317, 318; 359/386
See application file for complete search history.

(56) References Cited

U.S. PATENT DOCUMENTS

| | | | |
|---|---|---|---|
| 2001/0045523 | A1 | 11/2001 | Baer |
| 2002/0141052 | A1 | 10/2002 | Iketaki |
| 2004/0095576 | A1* | 5/2004 | Wolleschensky .............. 356/317 |

FOREIGN PATENT DOCUMENTS

| | | |
|---|---|---|
| DE | 10 2004 034 962 A1 | 2/2006 |
| WO | WO 2007/009812 A1 | 1/2007 |

OTHER PUBLICATIONS

Klar, Thomas A., et al.; "Breaking Abbe's diffraction resolution limit in fluorescence microscopy . . . "; Physical Review E. 2001; 64(066613):1-9.

* cited by examiner

*Primary Examiner* — David Porta
*Assistant Examiner* — Marcus Taningco
(74) *Attorney, Agent, or Firm* — Duane Morris LLP

(57) ABSTRACT

A method and arrangement for collimated microscopic imaging, including a first illumination of a sample in at least one region for exciting fluorescence, and a spatially resolving detection of the sample light by detector elements, the detection being associated with the region, wherein by means of a second illumination a sub-division of the region into separate fluorescent partial regions occurs, which are associated with the detector elements. The separation of the partial regions is carried out by the spatial separation of the fluorescent regions by means of intermediate regions having reduced fluorescence or no fluorescence, and/or by means of different spectral properties of the fluorescence from the partial regions.

30 Claims, 17 Drawing Sheets

FIG. 3
camera (pixel + light distribution)
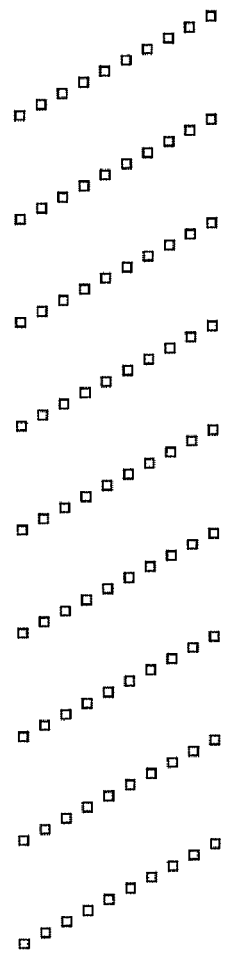
object point correlation in scanning steps 1-10
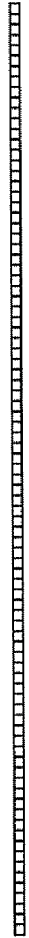
resulting line image
repetition of procedure after y-scan step
. . .
resulting 2-D image lateral light distribution in object plane axial light distribution in object plane axial light distribution in object plane and axially structured switching light distribution e.g., Fig. 7B or C + 477 nm resulting axial light distribution in object plane X: +/−1. diffraction order of S1 in Fig. 11

XX: =. diffraction order of S1 in Fig. 11 + S2,S3

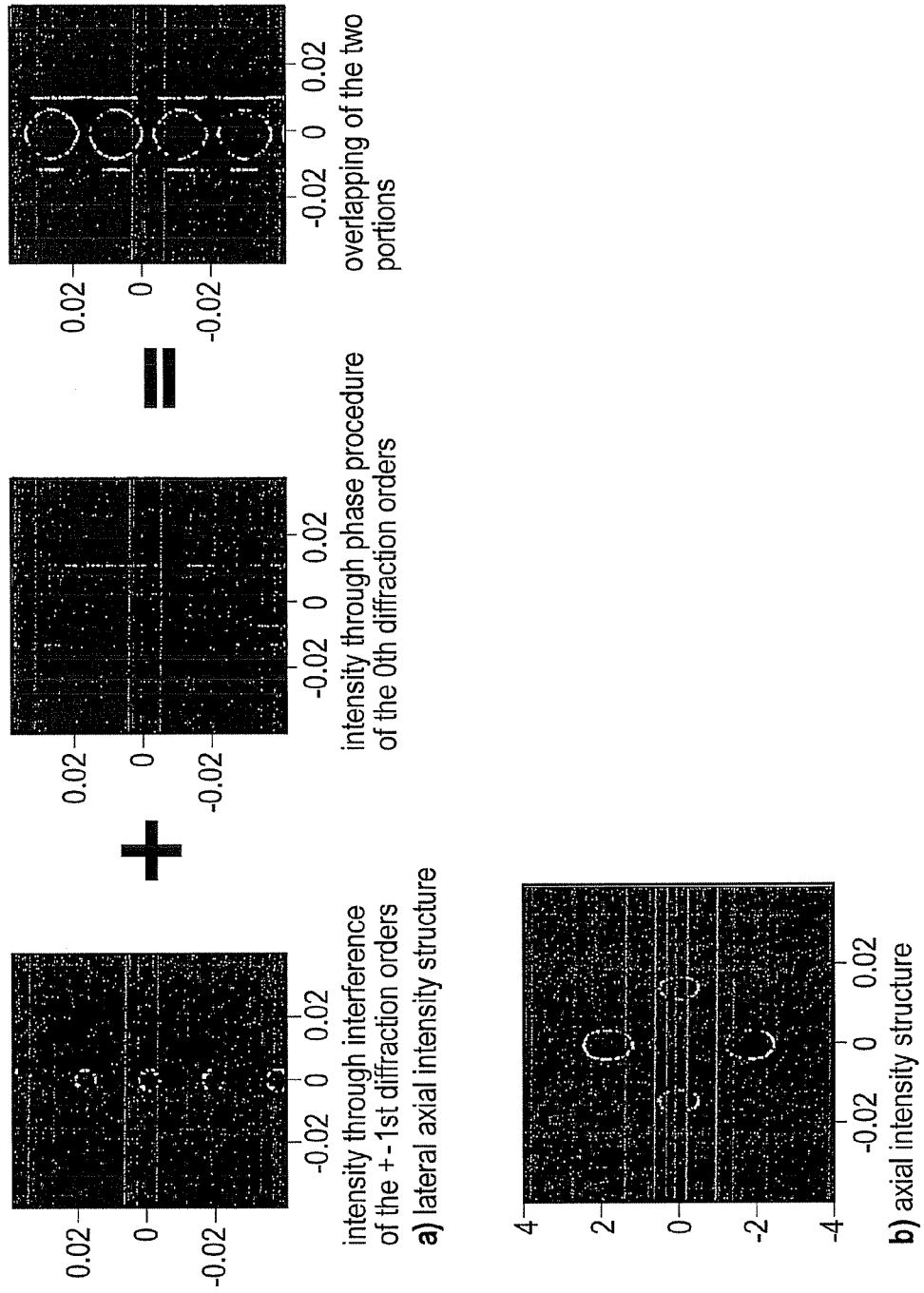

METHOD AND ARRANGEMENT FOR COLLIMATED MICROSCOPIC IMAGING

RELATED APPLICATIONS

The present application is a continuation of application Ser. No. 12/444,290 filed on Apr. 3, 2009, now abandoned which is a U.S. National Stage Application of International PCT Application No. PCT/EP2007/008556 filed on Oct. 2, 2007, which claims benefit of German Application No. DE 10 2006 047 912.2 filed on Oct. 6, 2006, the contents of each are incorporated by reference in their entirety.

FIELD OF THE INVENTION

The present invention relates to methods and arrangements for microscopic imaging with structured illumination. Increased spatial resolution is achieved by means of nonlinear interactions between samples, which is known from the prior art. By means of the method and the corresponding arrangements of this invention, this sample interaction is made use of for imaging in such a way that confocal imaging is possible with a resolution that goes beyond the diffraction boundary in all spatial directions with parallel data acquisition.

PRIOR ART

The prior art discloses various nonlinear sample interactions which can lead to enhanced spatial resolution when suitably implemented, specifically:
1. De-excitation of the excited level through stimulated emission (Stimulated Emission Deletion—STED), Klar and Hell, Opt. Lett. 24 (1999), 954-956
2. Depopulation of the ground state by triplet occupation (Ground State Depletion—GSD), Hell and Kroug, Appl. Phys. B 60 (1995). 495-497
3. Reversible or irreversible dye switching between a fluorescing state, a non-fluorescing state, a reduced fluorescing state, or a fluorescing state characterized by other features (such as a different emission wavelength), Hell, Jakobs and Kastrup, Appl. Phys. A 77 (2003), 859-860.

OBJECTS

The basic idea behind the method of the invention is that the dye is either
  a) brought to a non-fluorescing or slightly fluorescing state in a spatially limited region so that a subsequent excitation can lead to fluorescence only, or predominantly, in a limited region (second and third method), or
  b) is de-excited in a spatially limited region following excitation so that fluorescence is carried out only from a limited region (first method).
In both cases, the intention is to achieve a fluorescing region which is smaller than that which can be achieved by diffraction-limited excitation.

The basic principle is illustrated in FIG. 1 with the steps and schematically depicted spatial distributions which are used or which result. The arrangements known from the prior art are based on point scanning methods in which light distributions with zero settings in the center (doughnut modes, as they are called) which are preferred for depopulation, switching and de-excitation are applied. The laser beam is scanned over the sample and the steps shown in FIG. 1 are carried out sequentially in every spatial point. Previous arrangements according to the first method (e.g., Klar et al, PNAS 97 (2000), 8206-8210) and third method (Hoffmann et al., PNAS 102 (2005), 17565-17569), all of which function according to the scheme mentioned above, have been described. A decisive disadvantage of this arrangement is the sequential data acquisition. Owing to the fact that the increased spatial resolution results in reduced excitation volumes, the fluorescence emission is reduced so that the pixel integration time must generally be longer (with a fivefold increase in resolution only laterally, the expected fluorescence emission is about twenty-five times lower, e.g., with a homogeneous dye distribution over the extent of diffraction-limited excitation). Further, some known switchable dyes such as Dronpa can be switched only with limited light power so as to afford many switching cycles (Habuchi et al., PNAS 102 (2005) 9511-9516). In this case, the third method mentioned above requires a considerably longer exposure time per pixel for switching off than that required for fluorescence excitation alone.

Therefore, it is clear that a parallel data acquisition is needed in order to arrive at acceptable image compilation times. In this connection, it must be taken into consideration that confocal imaging is required in order to avoid a loss of contrast and reduced resolution enhancement due to extrafocal fluorescence. A possibility offered by the prior art for parallelizing is simultaneous excitation with a plurality of spots, each of whose fluorescence characteristics are modified by a doughnut-shaped illumination. However, the doughnut-shaped illumination must lead to a nonlinear sample interaction, i.e., a saturation, in order to achieve increased resolution. This means that a relatively large area around the individual spot interacts with this light distribution, which only allows a low density of the spot and, therefore, meager parallelization. Further, a confocal detection in a multi-spot arrangement of this kind is cumbersome in technical respects.

SUMMARY OF THE INVENTION

A method and an arrangement in which a high-resolution image is achieved directly (without image processing) with parallel data acquisition is described in the following. The extrafocal background can be eliminated by variable confocal detection. This method and arrangement prevent the above-mentioned disadvantages of the multi-spot arrangement according to the prior art. In particular, an optimal parallelization (maximum density of the simultaneously excited regions of the sample) and a relatively simple technical implementation are made possible by the invention.

BRIEF DESCRIPTION OF THE DRAWINGS

The present inventions will be described in greater detail, using examples with reference to the annexed drawings, in which:

FIG. 3 illustrates the camera pixels and light distribution, object point allocation in the scanning steps, the resulting line image, and the resulting two-dimensional image after a Y-scanning step;

FIG. 18(a) illustrates an intensity structure; and

FIG. 18(b) illustrates an axial structuring of the illumination light in the object plane.

DESCRIPTION OF EMBODIMENTS

Basic Principles

An arrangement which meets the demands mentioned above is based on a line-shaped excitation and confocal detection by means of a line camera behind a slit diaphragm. By means of a suitable exposure pattern in combination with the nonlinear sample interaction, a de-excitation/depopulation/switching (always referred to hereinafter, by way of example, as switching) is realized in such a way that only a series of spots along a line can emit fluorescent light. The distance between these spots is at least as great as (but advantageously no greater than) the diffraction-limited resolution of the optical system. A possibility for generating an illumination of this kind (which is simultaneously also axially structured) consists in the diffraction of coherent light at a periodic structure and interference of the diffraction orders in the object plane, as is described in the application DE102004034962A1 which is hereby incorporated in the present disclosure. This results in diffraction-limited light distributions on the camera line which are separated from one another, impinge on corresponding pixels and are detected separately at the latter (see FIG. 2).

Figure 2:
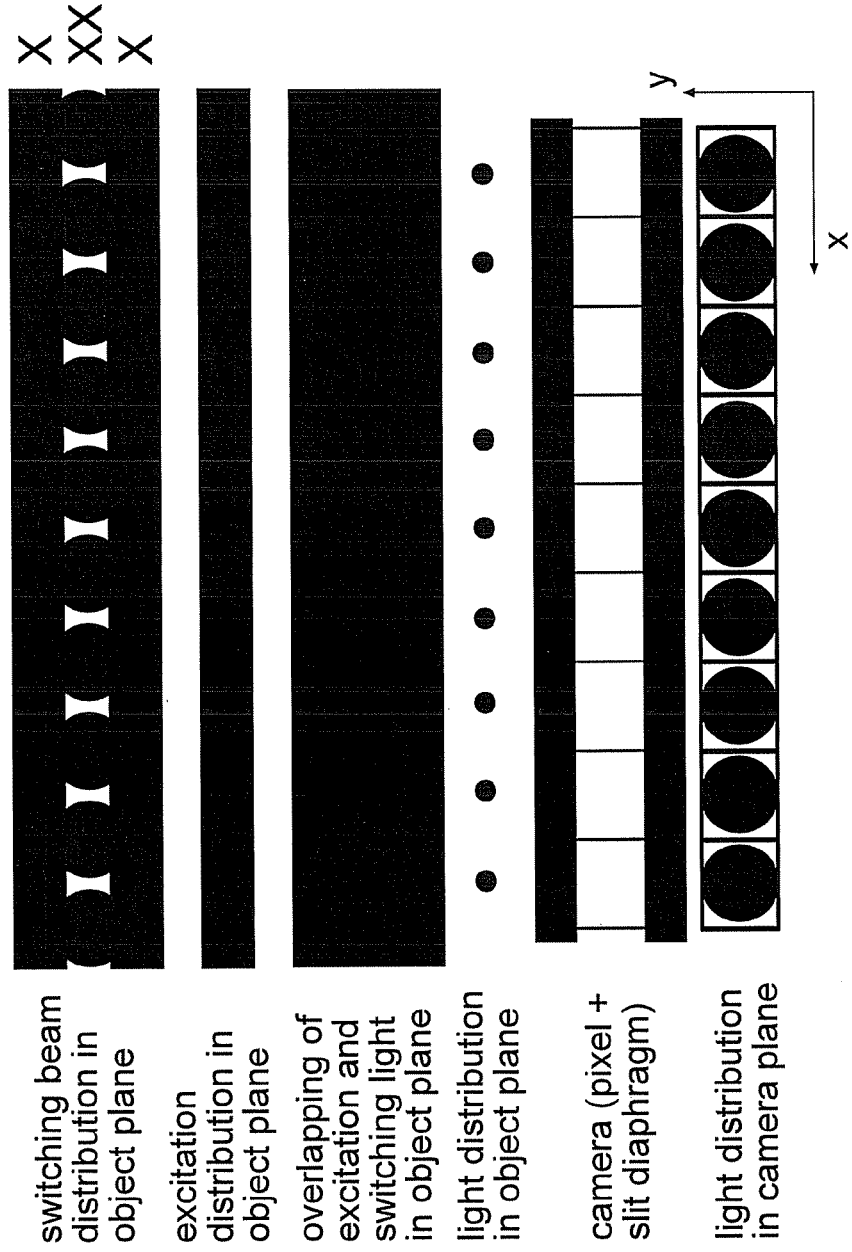
FIG. 2 is a diagram illustrating the switching beam distribution.

FIG. 2 shows, from top to bottom, the switching beam distribution in the object plane, the excitation distribution in the object plane, the superposition of excitation and switching light in the object plane, the camera pixels, and the light distribution in the camera plane. In the switching beam distribution, X represents the zeroth diffraction order referring to the diagram and description in FIG. 9 a) and FIG. 11. XX is the +/- first diffraction order according to the diagram and description in FIG. 9 a) and FIG. 11.

A highly resolved image is now obtained by scanning the object along line (x) and perpendicular to line (y). This scanning can be carried out by moving the illumination distributions, e.g., by means of a galvanometer scanner and/or by moving the object. In the former case, the illumination beam and the detection beam must pass over the same beam deflection elements in order to obtain a stationary light distribution on the detector (descanned detection). In case the object is simply moved (object scanning), the light distributions are stationary in every case.

The information about the correlation of pixel to measurement point on the sample is derived in a definitive manner from the scanning movement and the corresponding optics. This will be described more exactly: the image field raster observed by the detector is determined by the imaging of the camera pixels on the sample. For example, 512 pixels are imaged on the sample in such a way that every pixel detects an image surface of 1.5-times the diffraction-limited resolution (for an objective with an NA of 1.4, this corresponds at a wavelength 488 nm to a field of 488 nm/(2*1.4)*1.5=260 nm edge length). Adjustment of the illumination pattern (switching light distribution) ensures that there is a unique correlation between the luminous spots in the sample and the camera pixels. By means of the relative movement of the object and illumination pattern, different sample points are imaged. For this purpose, the scanning movement and the detection of the spot size in the sample which is synchronized with the scanning movement must be adapted. Typically, scanning is carried out with one half of the spot diameter (Nyquist theorem). Thus when a fivefold increase in resolution (N=5) is achieved in the example given above by mean of the nonlinear sample interaction, a sample scanning must be carried out at a distance of 260 nm/(5*2)=26 nm. Therefore, N*2 scan/detection steps (10 in the example above) are needed to completely scan a line. Therefore, 512*2*N highly resolved data points are obtained from 512 pixels in x-direction (see FIG. 3).

FIG. 3 shows, one below the other, the camera pixels and light distribution, object point allocation in scanning steps 1 to 10, the resulting line image, and the resulting two-dimensional image after a Y-scanning step.

Figure 4:
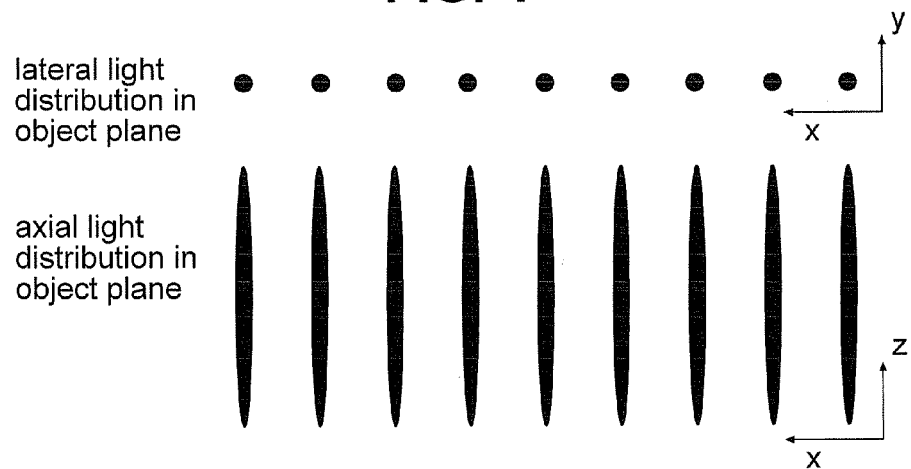
FIG. 4 shows the lateral (X/X) and axial (optical axis Z) light distribution in the object plane.
Figure 5:
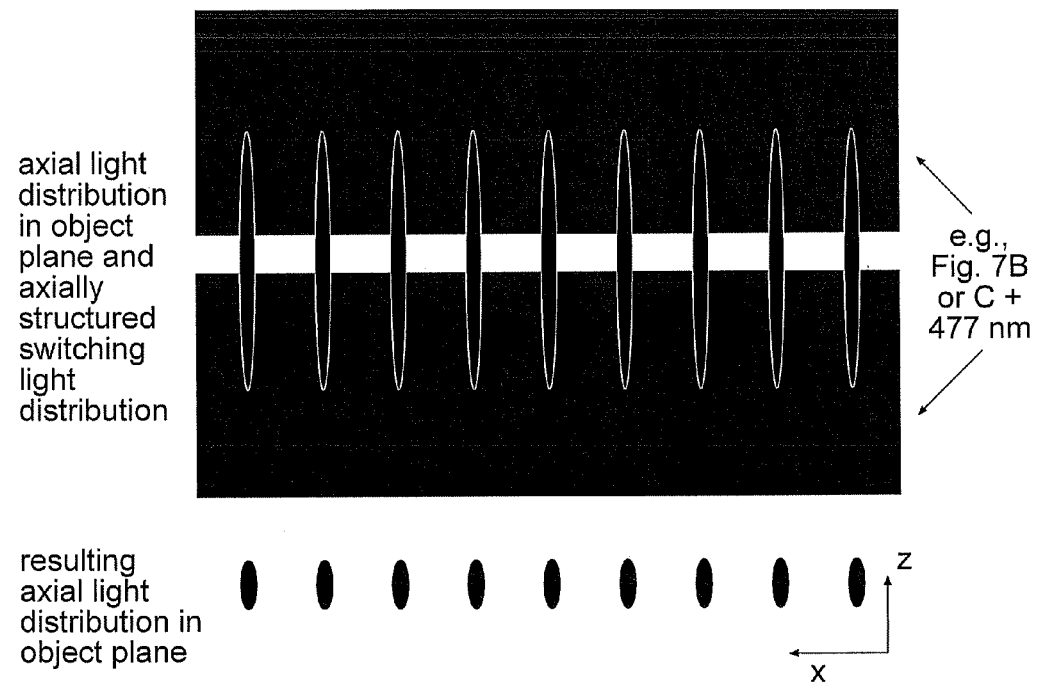
FIG. 5 schematically shows the axial light distribution which would occur without axially structured switching light, together with the axial structuring of the switching light.

The discussion has so far been limited to one object plane. However, objects are always three-dimensional. This has several consequences. For one, aside from the fluorescence in the focus with increased resolution, fluorescence is also excited outside of the focus. This fluorescence interferes with the imaging described above and can make it impossible to correlate the pixels to high-resolution object points. A remedy is afforded by confocal detection which effectively suppresses extrafocal fluorescent light. In the case presently under consideration, this is realized by means of an (ideally) variable slit diaphragm in front of the camera parallel to the line. On the other hand, the three-dimensional point spread function (PSF) must be taken into consideration for imaging. This will depend upon the switching light distribution as well as on the excitation PSF and detection PSF. In axial direction, the PSF can correspond to the diffraction-limited PSF (structured switching light only in lateral direction). FIG. 4 shows the lateral (X/X) and axial (optical axis Z) light distribution in the object plane. However, an axial resolution enhancement can also be achieved (FIG. 5) by means of additional structuring of the switching light in axial direction. FIG. 5 shows schematically the axial light distribution which would occur without axially structured switching light, together with the axial structuring of the switching light. The switching light distribution results, e.g., from the use of an optical element from FIG. 8 b) or FIG. 8 c) in an arrangement according to FIG. 12 (including the associated descriptions). The light distribution actually obtained in this case is shown at the bottom in FIG. 5. Depending upon the application, a distribution such as that in FIG. 4, bottom, or FIG. 5, bottom, can be useful. Therefore, it is advisable to be able to implement both scenarios in one device.

In principle, all of the above considerations can also be applied to a two-dimensionally structured switching beam distribution and detection with an area detector. In this case, the excitation and the switching on which may possibly be necessary are carried out with (far-field) area illumination. An arrangement of this kind would have the advantage of increased parallelism (e.g., $512^2$ points could be exposed simultaneously), but also has the disadvantage of non-confocal detection. The occurrence of extrafocal fluorescence can pose a severe problem depending on the sample (particularly with thick, strongly dyed samples).

Figure 6:
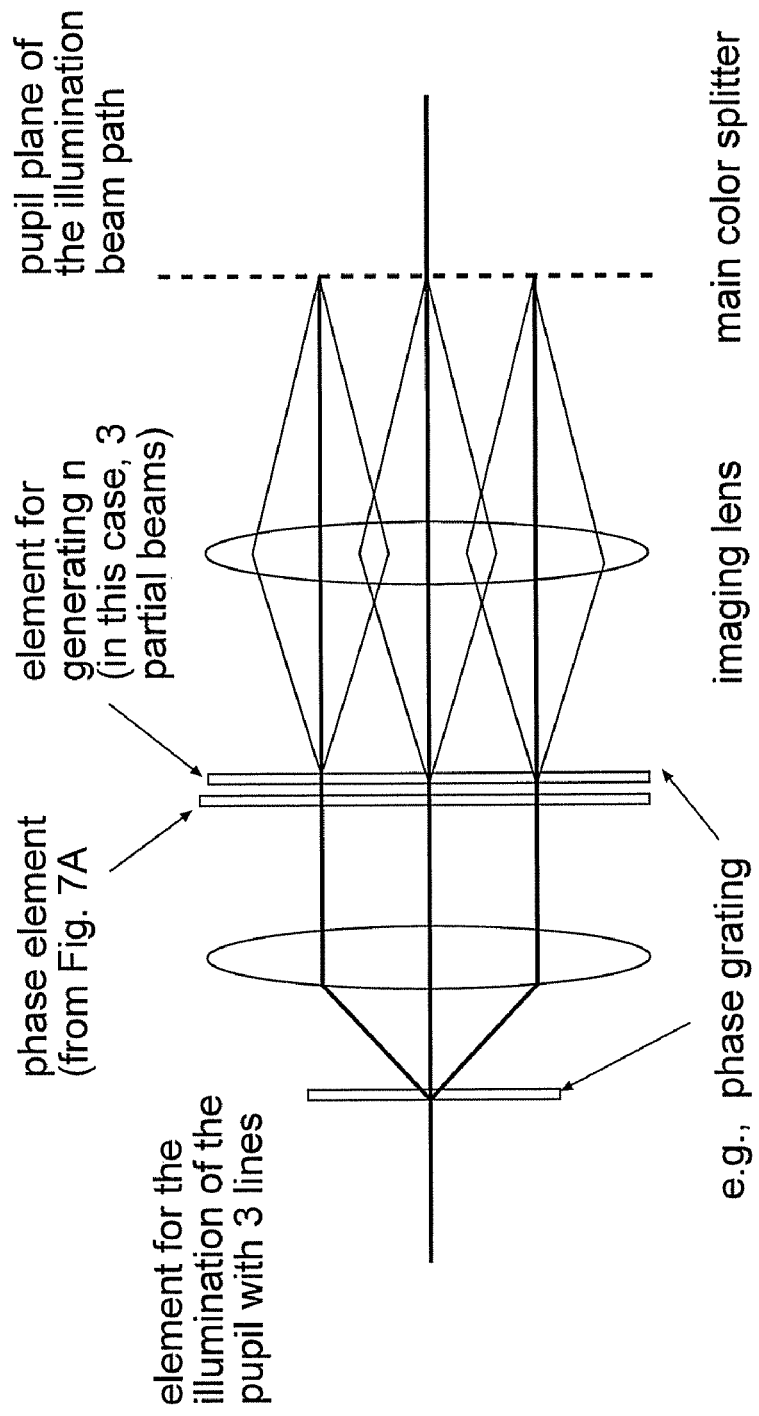
FIG. 6 is a schematic optical diagram which shows splitting in only n=3 lines.

An option for the use of increased parallelism while simultaneously preserving a certain confocality of the imaging is to image a plurality of separate lines on the sample and to carry out detection by means of an area detector. When the lines on the area detector are sufficiently separated (e.g., by about 10 pixels), a confocal detection can be achieved by selectively reading out the pixels associated with the lines. The confocality can be adjusted by also taking into account adjacent pixels. For example, by reading out the two pixel rows adjacent to the line and summing the corresponding associated pixel elements, the effective "slit diaphragm" can be increased by a factor of 3 with a corresponding decrease in confocality. The same elements in the vicinity of the pupil as those shown in FIGS. 8 and 9 can be used for an arrangement of this kind in the illumination beam path. However, the light must be split into n partial beams impinging in the pupil at different angles by means of an element arranged in front of the main color splitter. This results in n lines which are separated from one another in the object plane, every line being shaped in the same manner as shown in FIG. 4 and FIG. 5. An element, mentioned above, placed in front of the main color splitter can be a suitably shaped diffractive element (or a combination of a plurality of elements) with corresponding imaging or an arrangement for the geometric splitting and beam deflection of the partial beams. An example of this is shown in FIG. 6 which shows splitting in only n=3 lines for the sake of clarity.

Preferred Arrangement

Figure 7:
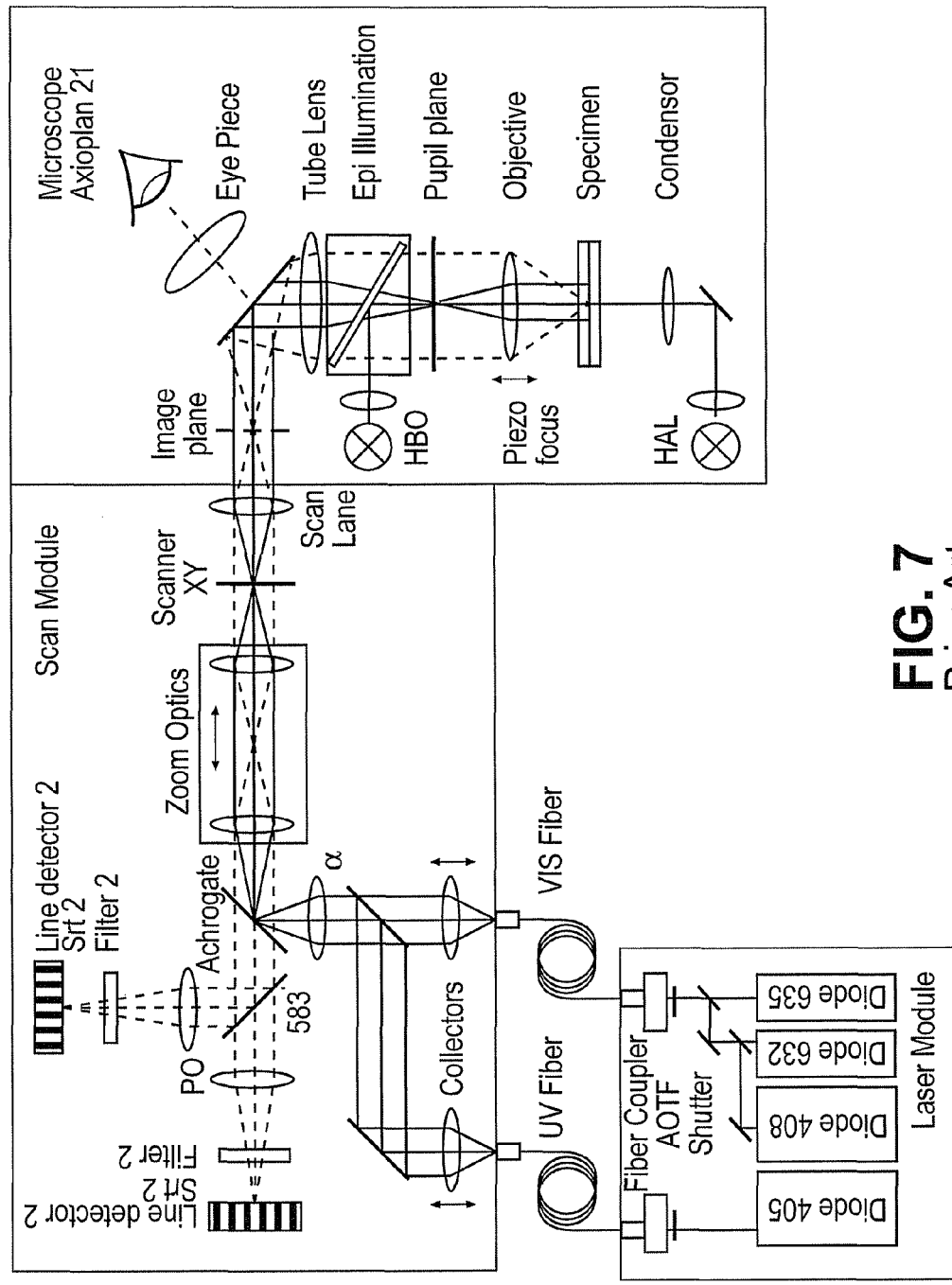
FIG. 7 schematically shows a modified line scanning arrangement.

A preferred arrangement uses a modified line-scanning system as shown in FIG. 7 and, for example, in DE 10257237A1 and EP1617271 A2 which are hereby incorporated in the present disclosure.

The modifications involve the following aspects:

The AchroGate achromatic color splitter is replaced by one permitting a structuring of the switching light in the object plane—this can be a suitable achromatic design or a dichroic beamsplitter.

The illumination unit is replaced by one which enables the required nonlinear sample interactions and the structuring of the switching light.

Figure 1:
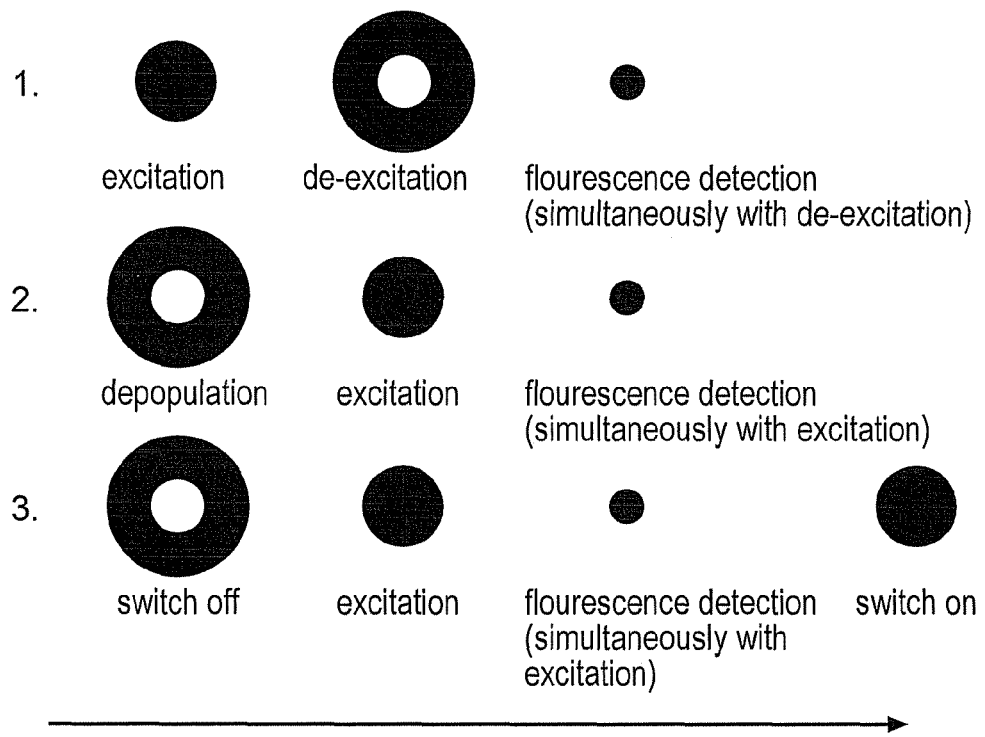
FIG. 1 is a diagram schematically illustrating sequential steps of known point scanning methods.

The illumination and the data acquisition are adapted in such a way that the exposure of the sample and the detection with the suitable sequence of switching/excitation/detection/switching on (see FIG. 1) is carried out within a suitable period of time.

The data evaluation is adapted so that a correlation of pixels to object points is carried out as shown schematically in FIG. 3.

Structuring of the Switching Light

Figure 8:
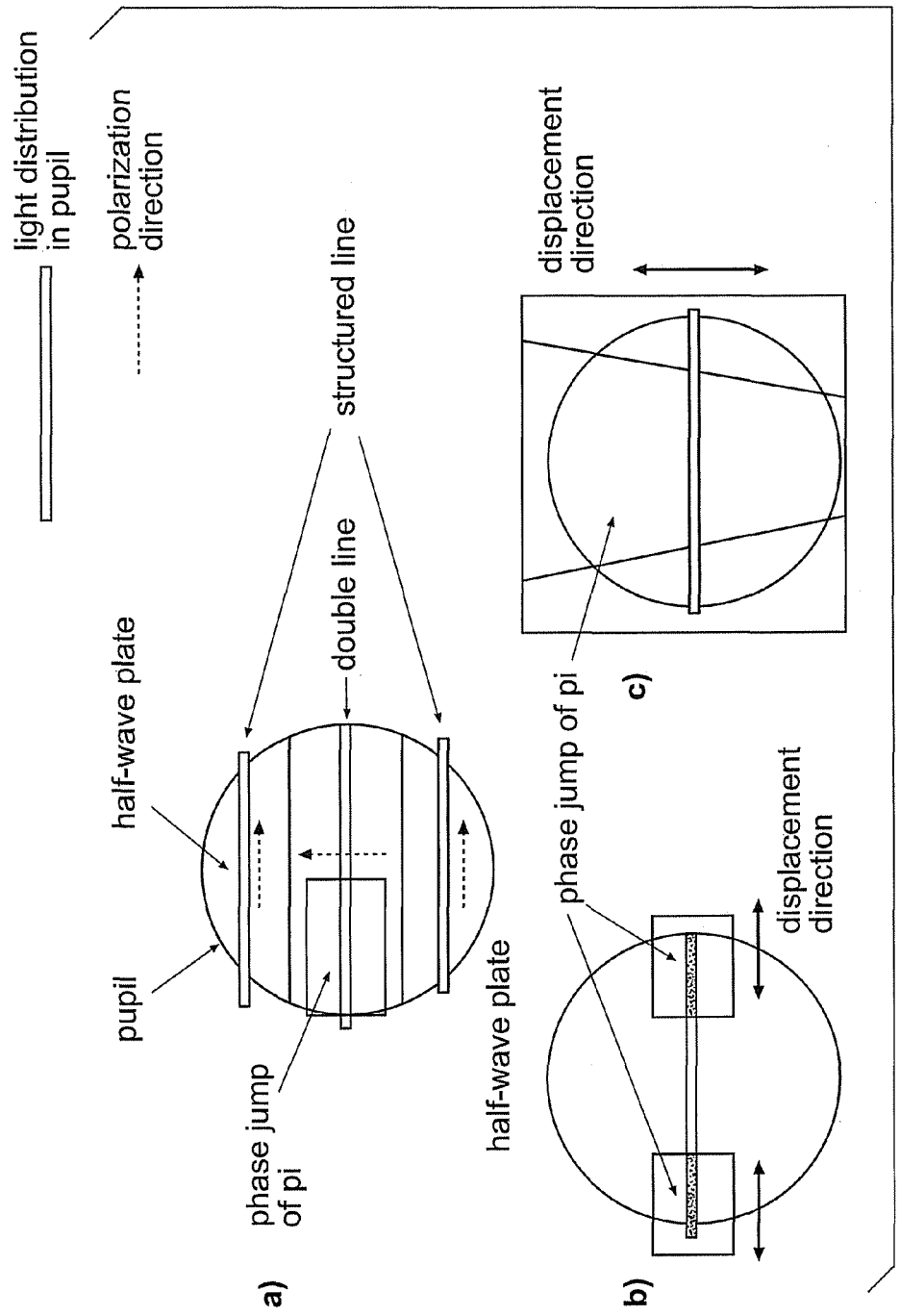
FIG. 8 illustrates a phase mask for lateral structuring.

A preferred way to generate a lateral structuring is made possible by means of a phase mask according to FIG. 8 a) which should be imaged in the vicinity of the pupil of the objective. In this connection, reference is had to the beam path shown in FIG. 12. The mask is divided in the middle, the right half and the left half producing different phase shifts in the light passing through. A double line—as is shown at the top in FIG. 2—is achieved by means of a phase jump of $\pi$ for half of the center line. A sine-shaped modulation of the line in the intermediate space of the double line (to produce a modulation of the excitation in the intermediate space of the double line, see FIG. 2, top) is generated by the interference of the two line distributions at the edge of the pupil. To achieve a modulation of the line at ⅔ of the limiting frequency, for example, the lines must have a spacing equal to ⅔ of the diameter of the pupil radius. It is important that the components of the light which generate the double line and those which generate the modulated center line overlap incoherently in the sample. This can be ensured by delaying the arrival of the corresponding light components in the object by a time greater than the coherence length. However, it is preferable simply to adjust the polarization of the light components orthogonal to one another as is illustrated schematically by arrows in FIG. 8. This can be accomplished, e.g., by means half-wave plates which selectively rotate the light in the outer area of the pupil (see FIG. 8). A suitable phase grating can be used in the vicinity of a conjugate image plane in front of the mask in order to obtain the distribution of the light on the phase mask shown in FIG. 8a). The center line then corresponds to the zeroth diffraction order, and the two lines at the edge of the pupil correspond to the first diffraction order of the corresponding grating. The optimal position of the light distributions in the object plane relative to one another is ensured at the same time through the use of diffraction orders of a grating. Because of the incoherence of the first diffraction orders relative to the zeroth diffraction order that is achieved by the steps described above, it is also ensured that the center line in the object plane can be modulated up to the limiting frequency of the imaging of incoherent light (which is twice as great compared to imaging with coherent light). Another consequence consists in that no structuring of the light is carried out in axial direction, in contrast to the arrangement described in DE102004034962 A1.

If an axial structuring of the switching light—as is shown schematically at the top of FIG. 5—is also desired, another partial beam of the switching light is modified with a phase mask according to FIG. 8 b) located in the vicinity of a plane conjugate to the objective pupil.

Masks 8 b) and 8 c) have a central region symmetric to the optical axis and to an axis perpendicular to the optical axis which produces a different phase delay of the passing light compared to the outer regions to the right and left sides. A phase delay of π of an outer portion of the line-shaped pupil illumination relative to an inner portion of the line-shaped pupil illumination is carried out. In theory, the optimal radius of the phase jump is $1/\sqrt{2}$ of the pupil radius of the objective. In practice, a somewhat smaller radius is often optimal. A phase plate such as that shown in FIG. 8 c) is suitable for optimizing the radius. Adaptation of the radius can be carried out by translation.

Figure 9:
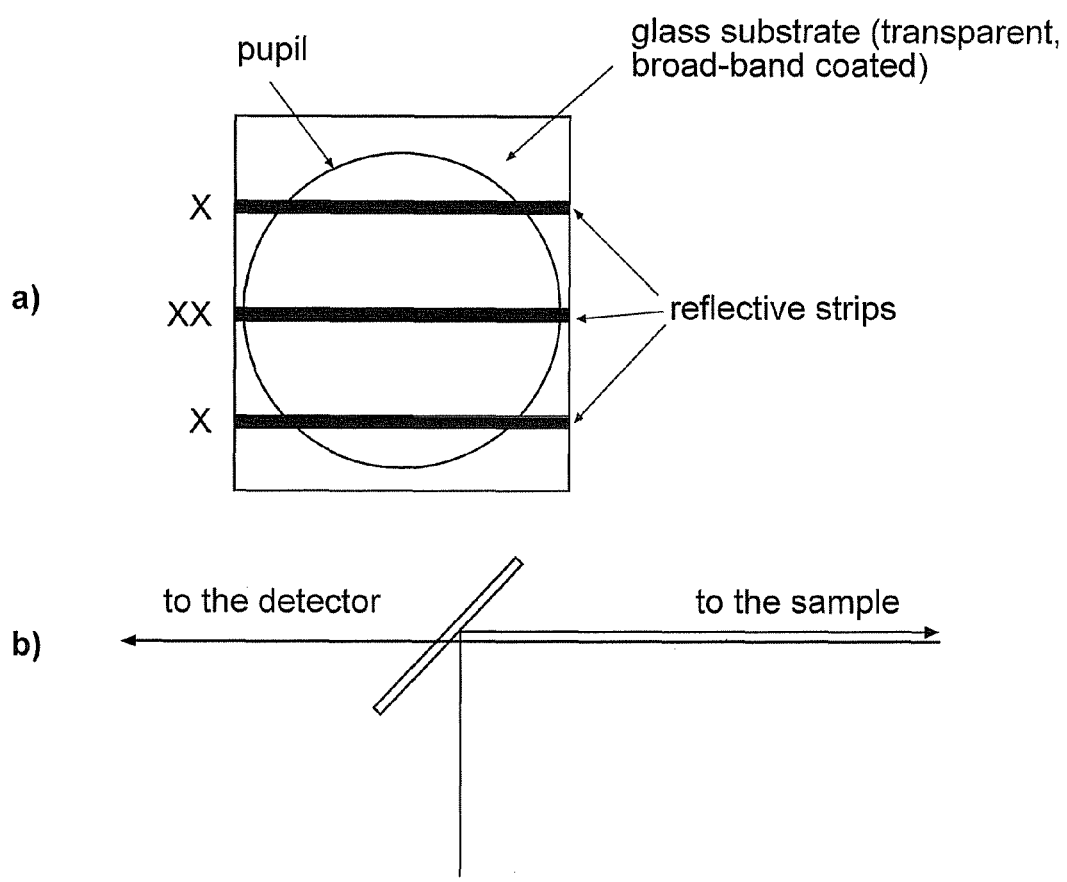
FIG. 9(a) illustrates an achromatic color splitter which results from the pupil light distributions in FIG. 8.
FIG. 9(b) illustrates the achromatic color splitter located in the beam in a conjugate pupil plane.

FIG. 9 a) shows an achromatic color splitter which results from the pupil light distributions in FIG. 8 and which is also compatible with the distributions for excitation and switching on (lines). This achromatic color splitter is located in the beam in a conjugate pupil plane as is shown in FIG. 9 b). The fluorescent light emitted by the sample fills the pupil and therefore passes the splitter (except at the reflecting strips). The outer mirror surfaces (X) are used for transmitting the +/− first diffraction order of S1 in FIG. 11, the inner mirror surface (XX) is used to transmit the zeroth diffraction order of S1 in FIG. 12 and the beam paths S2, S3. It must be ensured, as the case may be, that the mirror surfaces do not all lie in the same focal plane. In case the Rayleigh range of the light focused in this plane is less than the focus deviation of the outer mirror surfaces, the defocusing due to the magnification of the outer mirror surfaces (which are not in the focus) compared to the inner mirror surface must be taken into account.

Figure 10:
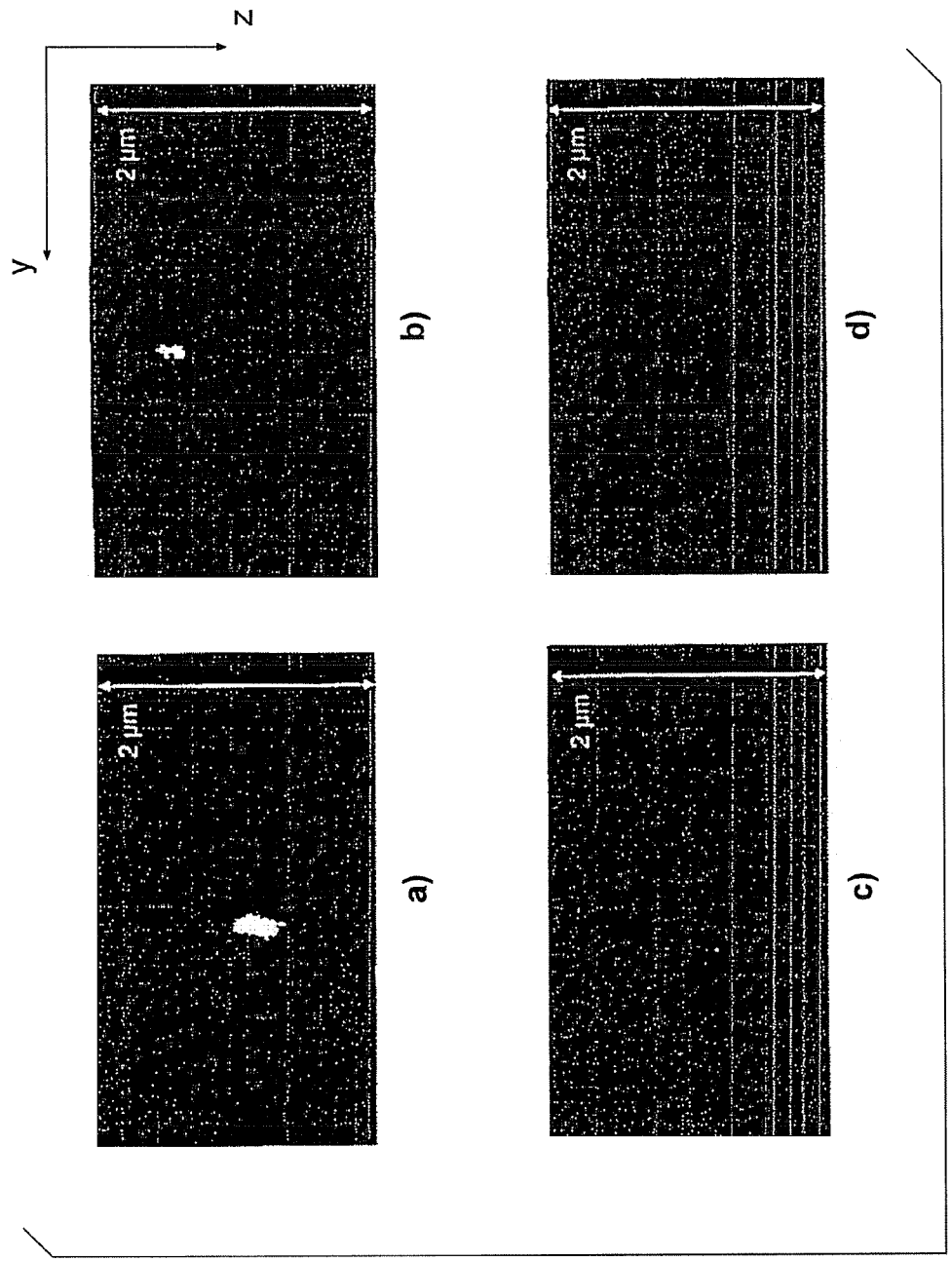
FIG. 10(a) shows the distribution without a mask (corresponds to excitation distribution)
FIG. 10(b) shows the distribution with a mask according to FIG. 8(b)
FIG. 10(c) shows the distribution with a mask according to FIG. 8(a)
FIG. 10(d) shows incoherent overlapping results in the distribution shown.

FIG. 9 shows experimental results (sections through the light distributions in the sample) with the corresponding masks with an oil-immersion objective having a numerical aperture (NA) of 1.4 at 488 nm. FIG. 10 a) shows the distribution without a mask (corresponds to excitation distribution), FIG. 10 b) shows the distribution with a mask according to FIG. 8 b), and FIG. 10 c) shows the distribution with a mask according to FIG. 8 a) (only the center portion). Finally, an incoherent overlapping results in the distribution shown in FIG. 10 d) which shows a minimum which is surrounded in the y- and z-directions. This minimum extends to about 170 nm (y) and 400 nm (z), which corresponds roughly to the inverse of the diffraction-limited limiting frequencies (lateral: $\lambda/(2 \cdot NA) \approx 170$ nm, axial: $\lambda/(n-\sqrt{n^2-NA^2}) \approx 520$ nm).

The point pattern of intensity minima occurring in the focus in the sample caused by a corresponding nonlinear sample interaction is a point pattern of excitable regions (GSD/switching) or of regions in which there is still significant excitation (STED). These regions are appreciably smaller after suitable exposure optimized for the dye (wavelength, intensity, exposure time) than a diffraction-limited light distribution and therefore allow a scanning of the sample with increased resolution. The adjustment of the illumination is carried out based on knowledge of the dye and can be optimized at the device based on the resolution of test structures (e.g., beads). Since this point pattern must be imaged exactly on the pixels of the line camera, a variable optical system (zoom) which makes it possible to adapt the periods of the pattern to the periods of the detector elements is advantageously provided in the illumination beam path or detection beam path. The position of the imaged spots (i.e., their center of gravity) can be centered within the pixels by means of another element such as a tiltable, thick glass plate in the illumination beam path or detection beam path (see, e.g., DE 102004034960A1).

Excitation and Switching On

The excitation and switching on are carried out with diffraction-limited light distributions which are generated without a mask. In the preferred embodiment example, these are lines which have the most homogeneous possible intensity curve along the line and extend in a diffraction-limited manner perpendicular to the line.

The excitation is carried out either before the switching/de-excitation (STED) or after the dye has been switched off (GSD/switching) by the switching light in a structured manner. Only in the case of switching is it generally necessary to subsequently reverse the switching off by a switch-on laser, because the other processes spontaneously revert to the initial state of the dye (see also FIG. 1 with respect to the timing). In case pulsed lasers are used (which is generally required in STED), the time sequence can be achieved by retarding the corresponding partial beams. When using continuously emitting (cw) lasers, the time sequence must be achieved by means of fast switches (preferably AOTFs).

The optimal parameters for excitation and switching on are determined beforehand from knowledge of the dye characteristics. For switching on, the aim is to reverse the switching off as completely as possible; optimized excitation and simultaneous detection of the emitted fluorescence signal is carried out by maximizing the signal-to-noise ratio. Different boundary conditions must be taken into account for the different interaction mechanisms:

With STED, only the number of excited molecules remaining after excitation and subsequent de-excitation can contribute to fluorescence. For a detection of photons going beyond the one-time emission of these molecules, it is necessary to repeat the process (excitation—de-excitation—fluorescence detection).

With GSD, excitation can be carried out and the resulting fluorescence detected only until the molecules spontaneously revert back from the triplet level. This is a comparatively short time period on the order of 1 µs.

When switching dyes, the excitation wavelength and the switching wavelength are identical in some cases. If this switching happens to be the switching off of the dye (as with Dronpa), the detection of fluorescence photons must be prevented during the targeted switching with the switching light distribution or separated from the detection of the photons from the spatially limited region. Further, the fluorescence signal can be detected only until the dye is switched off even in the spatially limited region. Otherwise, there are no other restrictions provided the dye remains stable in the switched off state. Even when the excitation wavelength and the wavelength for switching on the molecule are identical (as is known, e.g., for the asFP585 protein, Hoffmann et al., PNAS 102 (2005), 17565-17569), this does not pose any problems provided the fluorescence excitation is more efficient than the switching process and the excitation outputs, switching outputs and exposure times are adapted in a corresponding manner.

Generally, not all light-emitting molecules in a sample take part in the nonlinear sample interaction (STED/switching/GSD). This leads to a background signal which is not subjected to the nonlinear beam shaping and accordingly limits the high resolution that can be achieved. In case of long-lived states (i.e., approximately >1 µs) as in GSD and switching, the magnitude of the background relative to the signal of the molecules participating in the nonlinear sample interaction can be gauged by a further recording before switching on again (switching) or before the spontaneous relaxation into the ground state (GSD). This is because the unstructured excitation (S2, FIG. 11), e.g., in photoswitches such as Dronpa, in addition to the fluorescence excitation also leads to the switching off of the Dropna molecules (similarly the excitation also leads to an occupation of the triplet state in GSD). Therefore, in further (unstructured) excitation and detection, only those molecules which are not subjected to the photoswitching process (or GSD) emit light. The procedure is similar with switchable molecules in which the fluorescence excitation leads to the switching on of the molecule (as in asFP, Hoffmann et al., PNAS 102 (2005), 17565-17569). However, the dye must initially be switched off in an unstructured manner in an additional step in this case and the fluorescence excited by unstructured illumination is then detected.

EXAMPLE

Switching of the Dronpa Protein

Figure 11:
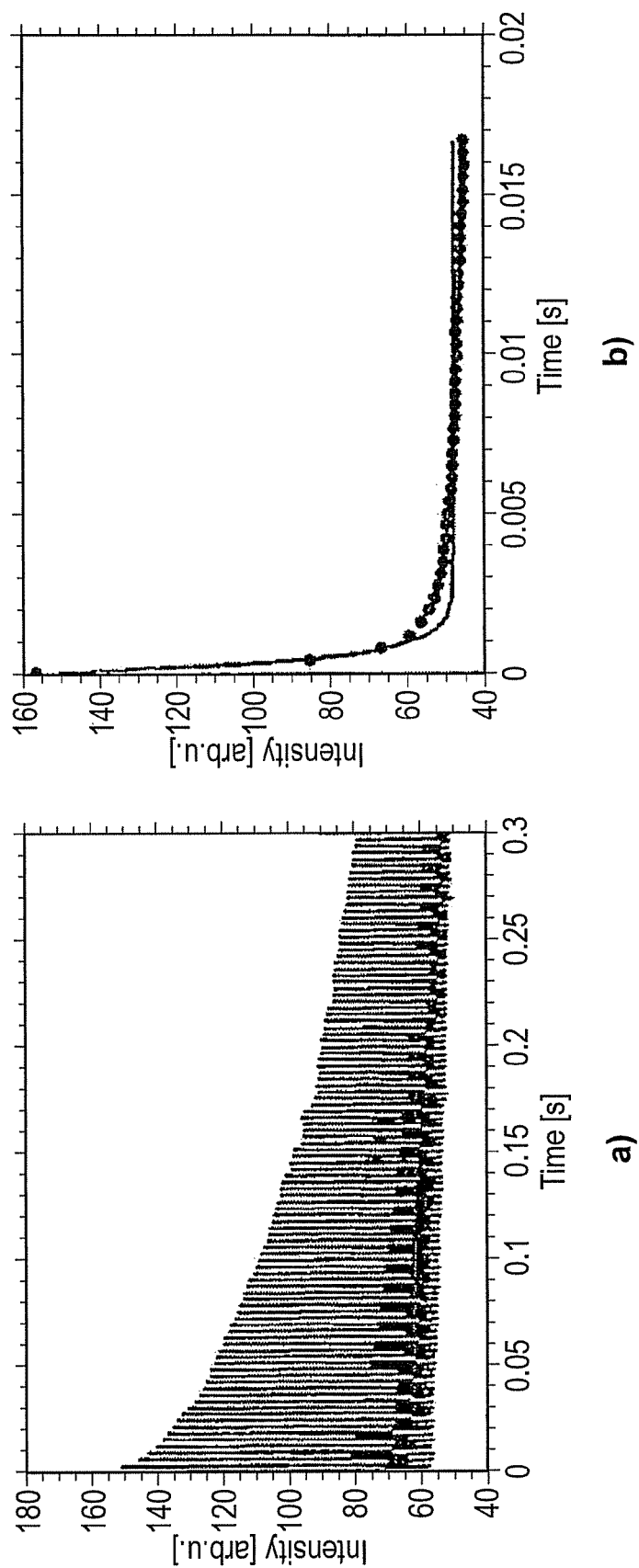
FIG. 11(a) is a graph illustrating intensity versus time showing switching on and off.
FIG. 11(b) is a graph illustrating intensity versus time showing switching off.

A suitable candidate for switching is the Dronpa protein (Habuchi et al., PNAS 102 (2005) 9511-9516). In this case, the switching off and the excitation are carried out with a wavelength in the range of about 450 nm to 520 nm. Switching on can be carried out in the range of 350 nm to 420 nm. This makes it possible to work, e.g., with the lines of the argon laser at 477 nm and 488 nm and to use a laser diode at 405 nm for switching on. The mutual switching on and off is shown in FIG. 11 a). A detailed view of switching off is represented in FIG. 11 b). This illustrates the long exposure times of about 5 ms for achieving a sufficient switching off. While the exposure time can be shortened by increasing the intensity, this would reduce the number of possible switching cycles compared to FIG. 11 a) in which about 100 switching cycles are shown.

Figure 12:
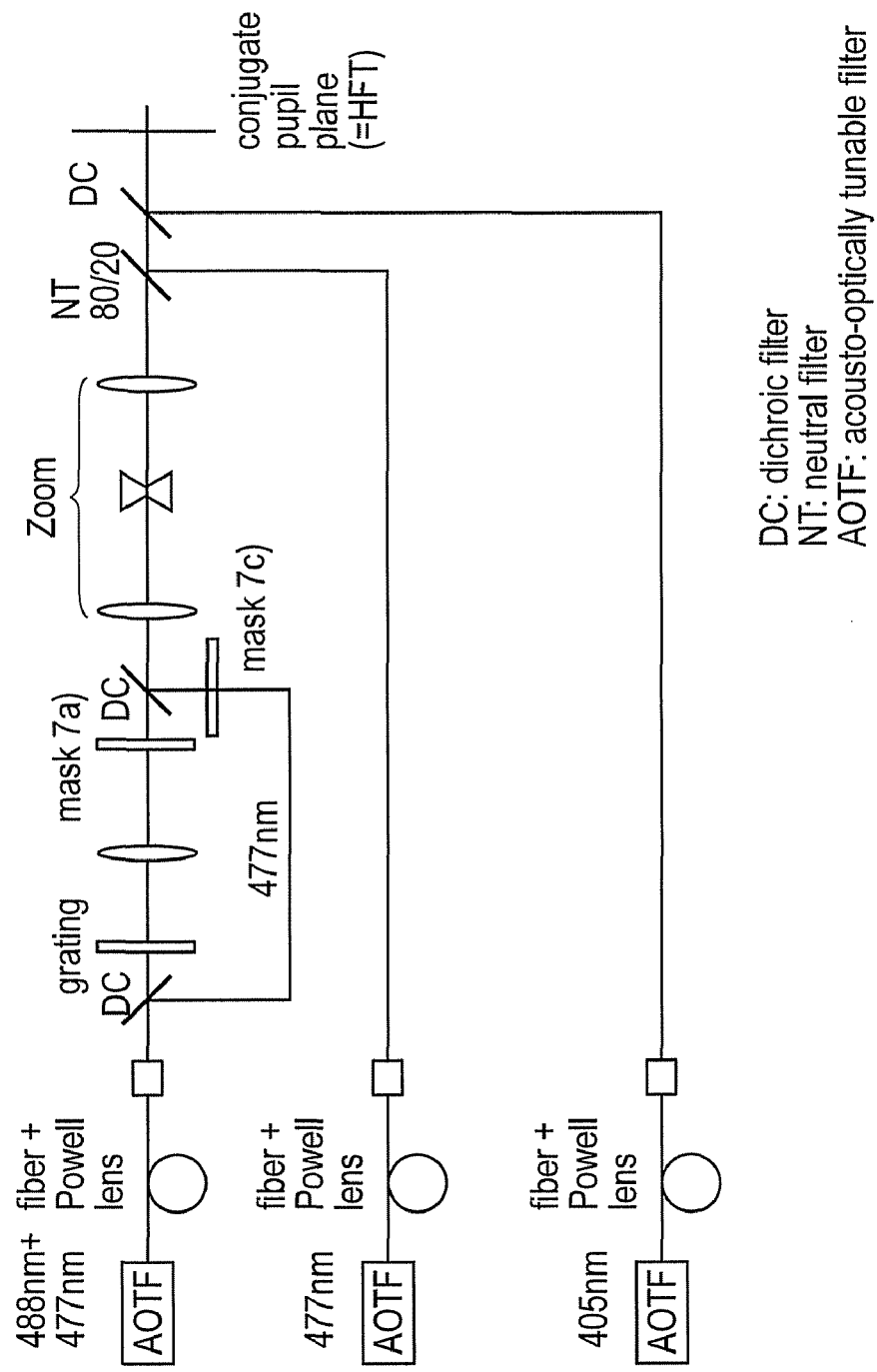
FIG. 12 is a schematic view showing a preferred illumination unit for a laser scanning microscope for use with Dronpa.

FIG. 12 shows a schematic view of a preferred illumination unit for a laser scanning microscope for use with Dronpa. S1 represents the beam path for generating the switching light distribution (see FIGS. 2, 7 and 5). The dye is switched on in this case either before switching off or after excitation. S2 is the excitation beam path, S3 is another beam path for switching on a switched off dye, if necessary. Accordingly, S1 (switching off) is carried out first, followed by S2 (excitation) and S3 (switching on) either at the very start or at the very end, wherein detection is carried out at S2. The wavelength 477 nm at S2 can also be replaced with another excitation wavelength (e.g., 488 nm).

STED and GSD (see the introductory part of the specification) can be realized by means of S1 and S2, STED can be realized by S2 followed by S1, and detection can be realized in S1, GSD by S1 followed by S2, and detection in S2. In S1, after the beam shaping (e.g., by means of a Powel lens) and after passing through a splitter DC in the zeroth diffraction order of a grating followed by the mask 7 a) (phase jump), the two laterally limiting outer lines of the switching beam are generated in the sample and the structuring of the center line is generated by means of the +/− first diffraction order.

The mask 7 b) or c) (after reflection at the splitter DC and separate beam path until after the mask 7c)) generates the limiting lines of the switching beam in axial direction by means of the phase jump described above.

Slightly different wavelengths (in this case, 488 nm, 477 nm) can be used for the beam paths through 7 a) and 7 c), but they must both lie within the range of the response behavior of the respective dye.

Figure 13:
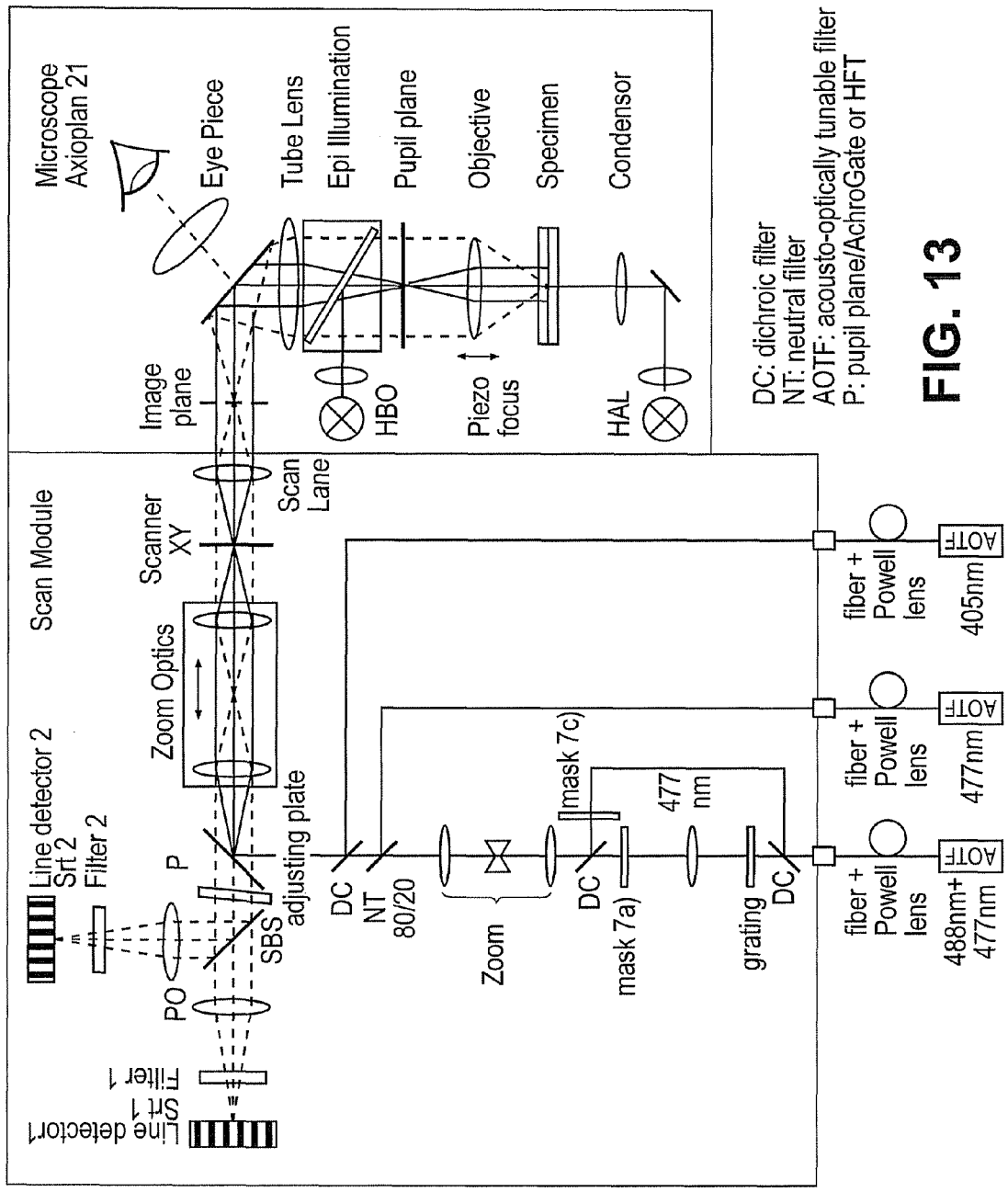
FIG. 13 shows the integration of an illumination unit according to the invention in a line-scanning microscope.

The integration of an illumination unit according to the invention in a line-scanning microscope is shown in FIG. 13. It contains the above-mentioned adjusting plate in the detection beam path for positioning the spot on the row of detectors. An additional zoom in the system serves to adjust the imaging of the illuminated line in the object on the row detectors. Accordingly, a selected portion of the line can be imaged on the row detectors. The definitive correlation of the illumination spot and camera pixels must be ensured in every case by the interaction of the two zooms.

In order to achieve a flexible system for switching additional dyes (also simultaneously with Dronpa), additional lasers are connected and the design of the dichroic splitter DC is provided for a plurality of colors (or as a neutral splitter). Further, it may be necessary (depending upon the wavelength difference) to change masks (although simultaneous operation would not then be possible).

Figure 14:
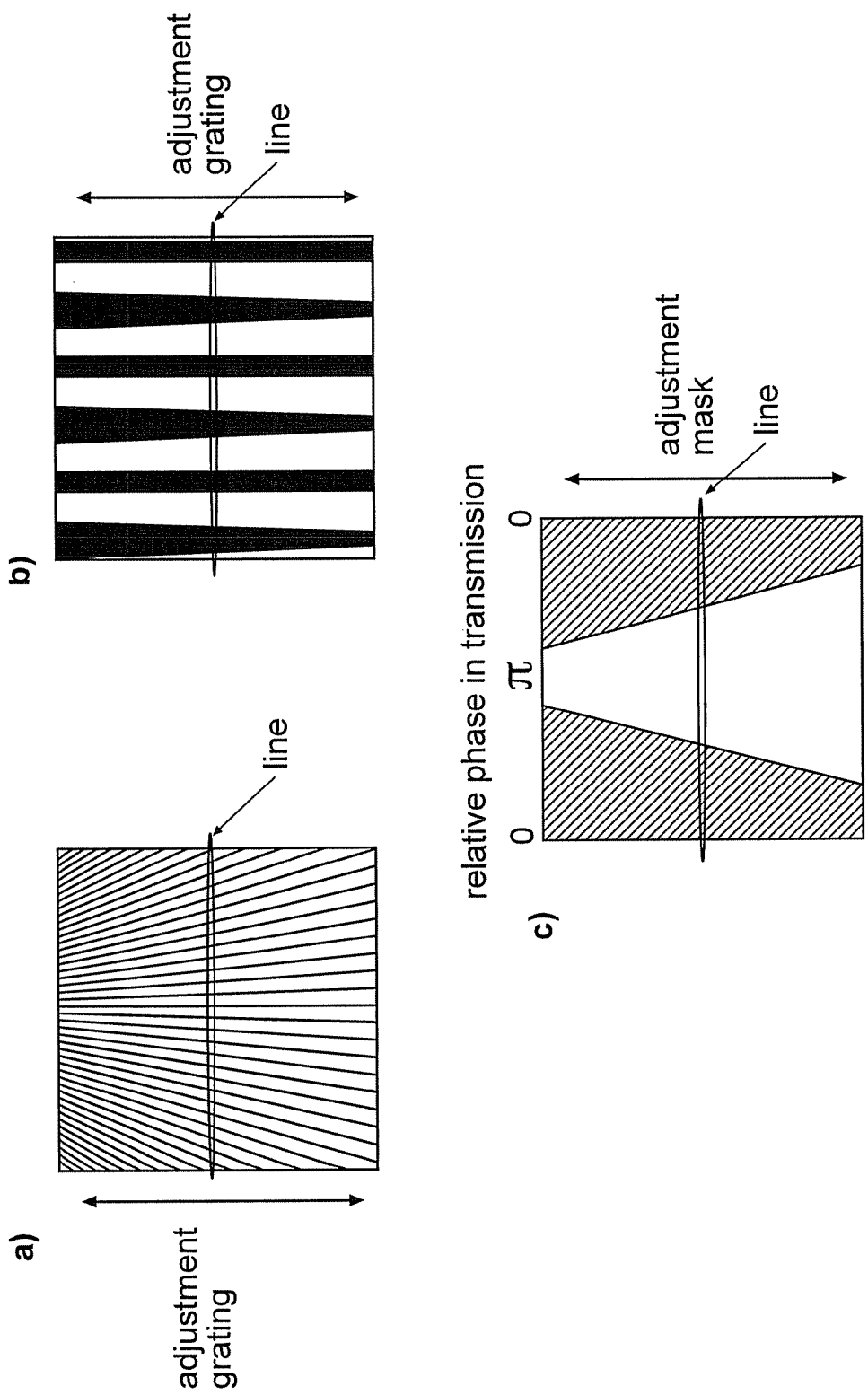
FIGS. 14(a)-(c) illustrate adjustment gratings for masks.

A simple adaptation consists in changing the grating constant so that the diffraction orders occur at the same location in the pupil. This can be achieved by a translation of a grating as is shown in FIG. 14 a). With moderate wavelength changes (on the order of 5%), the masks can also be used simultaneously with a plurality of wavelengths.

Also, when a wavelength is used, the use of different objectives, for example, creates the need for adjustment possibilities in the system. In this connection, a basic adaptation of the illumination to the different pupils of the objectives is carried out by means of the zoom system directly following the main color splitter (FIG. 8). Another specific adaptation is the relative proportioning of the intensity in the diffraction orders, which can result from the different losses of the orders when changing objectives. Further, this makes it possible to adapt specifically to the object. FIG. 14 b) shows a preferred form of adapting by changing the effective gap ratio at the grating while maintaining the same grating constant. Adapting the radius of the phase jump of the mask in FIG. 8 b) is particularly critical for optimal structuring in axial direction. A precision optimization of this radius, e.g., based on the recording of PSF, with the objective to be used is possible with a mask design such as that shown in FIG. 12 c). The effective radius of the phase edge can be adapted by translation of the mask.

Simulation of the Intensity Distribution for Dronpa

Figure 15:
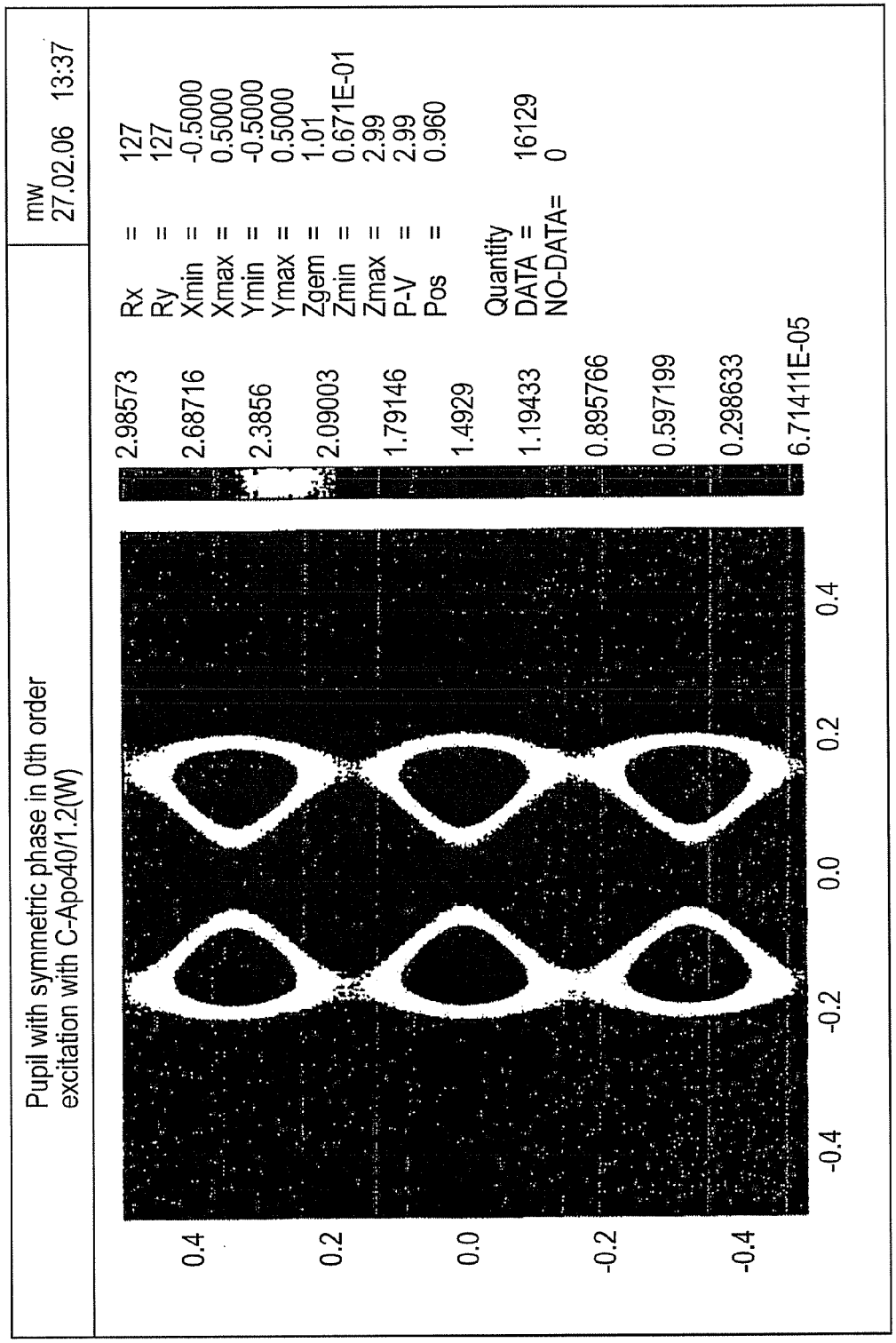
FIG. 15 shows the intensity distribution of the illumination in the object plane using the phase mask from FIG. 8(a).
Figure 16:
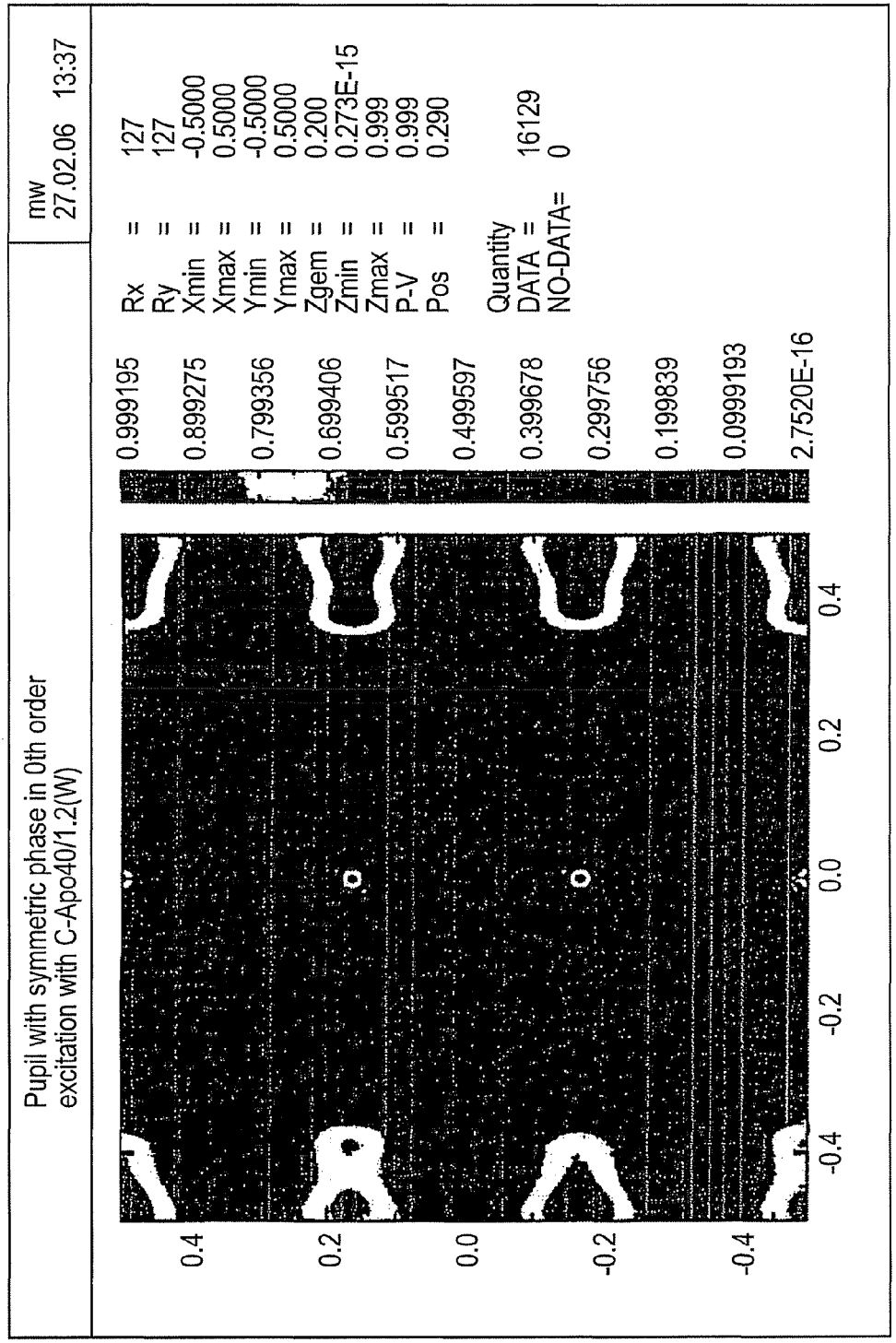
FIG. 16 shows a molecule population in the excited state with saturated switching off.

FIG. 15 shows the intensity distribution of the illumination in the object plane using the phase mask from FIG. 8 a). The quantity n of excited molecules decreases exponentially with the illumination intensity and the exposure duration. Using Dronpa as an example, FIG. 16 shows the resulting molecule population in the excited stated with saturated switching off, which provides a measurement for the PSF.

An Optical Embodiment Example

Figure 17:
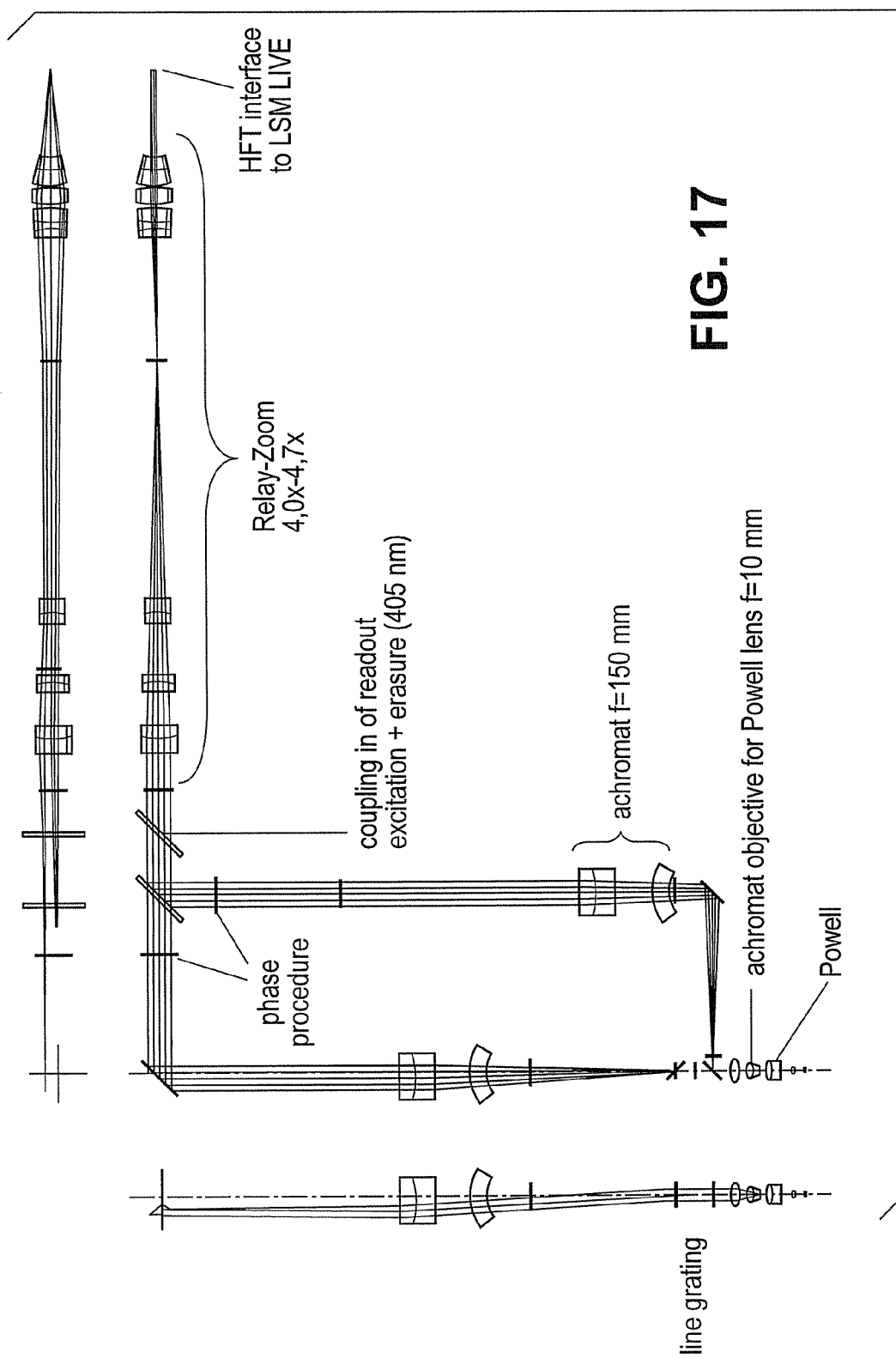
FIG. 17 illustrates an embodiment example of the illumination.

An embodiment example of the illumination is shown in FIG. 17. Side views of the beam path are shown at left and at the top.

A light bundle which is adapted to a Powell lens and has a Gaussian intensity profile is provided by fiber coupling. The light bundle has two wavelengths, 477 nm and 488 nm. The Powell lens (divergence 30°) generates a line-shaped illumination with a homogeneous intensity distribution along the line in the focal plane of the following achromatic objective with a focal distance of 10 mm. This plane is conjugate to the object plane of the microscope. A first color splitter splits the two homogenized laser lines. A light path, advantageously that with 488 nm, has a line grating with 55 l/mm which generates the zeroth and ±first diffraction orders in a determined intensity ratio of 8:1. These laser lines are imaged by 2f-imaging with 150 mm focal distance onto a phase element which is located in a plane conjugate to the microscope pupil. The phase element is described in FIG. 8 a). In the object plane, this phase element causes an intensity structure according to FIG. 18 a). The grating is advantageously formed as a phase grating. For precise adjustment of the intensity ratio between the zeroth and first diffraction order, the grating has a variable groove depth as is shown in FIG. 14 b). Since the illumination of the grating is line-shaped, the efficiency of the diffraction orders can be adjusted by lateral displacement of the grating. The second light path only has the same 2f imaging as the first, but without a grating. The phase procedure in the pupil of the second light path is implemented by a phase mask according to FIG. 8 c). This enables an axial structuring of the illumination light in the object plane (FIG. 18 b)). The lateral extension of the masks is about 12×12 mm$^2$. The diffraction orders in the first light path are at −4 mm, 0 mm and 4 mm. The two light paths are recombined after these procedures. The illumination pupil is adapted to the pupil of the microscope by means of relay optics. The interface is the main color splitter. The imaging scale of the relay optics is 4.35. The variability of the relay optics serves for precision adjustment of the imaging scale. The beam combiner is followed by a neutral splitter which serves to couple in the light for fluorescence excitation (477 nm) and also the light for erasing the structure impressed in the object (405 nm).

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for collimated microscopic imaging with a first illumination of a sample in at least one region for exciting fluorescence and a spatially resolving detection of the illumination of said sample illumination by detector elements associated with the region, comprising separating said region by a second illumination into separate fluorescing partial regions which are associated with said detector elements, wherein said separating of said region into partial regions comprises spatially dividing said fluorescing regions by means of intermediate regions with reduced fluorescence or no fluorescence and/or by different spectral properties of the fluorescence from said partial regions; and measuring a second illumination of said at least one region being carried out without a pattern, and detecting fluorescence excited by the first illumination in a spatially resolved manner.

2. The method according to claim 1, wherein the different spectral properties are a fluorescence of different wavelength or a different spectral distribution.

3. The method according to claim 1, wherein a reduction of the extent of the partial regions by de-excitation (depopulation) and/or switching the fluorescence state are/is carried out by said second illumination.

4. The method according to claim 1, wherein a reduction of the extent of the partial regions is carried out by means of nonlinear interactions of said second illumination with at least one substance capable of fluorescing which is present in the sample, and wherein
   (a) a de-excitation of an excited level is carried out by stimulated emission (STED) and/or
   (b) a depopulation of a ground state is carried out by triplet occupation (GSD) and/or
   (c) the at least one substance capable of fluorescing is driven from a state with first fluorescence characteristics into a state with second fluorescence characteristics or reduced fluorescence by reversible or irreversible optical switching.

5. The method according to claim 1, wherein a definitive correlation of the partial regions to the detector elements is carried out by optical imaging of the fluorescence emitted by the said partial regions onto the detector.

6. The method according to claim 1, wherein the partial regions are associated with the detector elements in such a way that the center of gravity of the partial regions is imaged substantially in the center of the detector elements.

7. The method according to claim 1, wherein an image obtained by measuring said second illumination of said at least one region is applied to an image recorded with enhanced resolution in order to achieve a reduction in the background signal in the image with enhanced resolution.

8. The method according to claim 1, wherein said region extends in a line-shaped manner.

9. The method according to claim 8, wherein an extension perpendicular to the line is diffraction-limited.

10. The method according to claim 1, wherein the second illumination has a patterned light distribution which comprises a periodic pattern along the direction of the illumination line and at least two laterally and/or axially limiting outer lines.

11. The method according to claim 1, wherein the fluorescent light which is excited outside a focus is suppressed by a variably adjustable slit diaphragm in front of the detector elements.

12. The method according to claim 1, wherein said region is formed of a plurality of line-shaped sub-regions which are spatially separated from one another.

13. The method according to claim 1, wherein the fluorescent light which is excited outside a focus is suppressed in an adjustable manner by a variable selection and a variable combination of detector elements.

14. Method for operating a fluorescence microscope, wherein a structured illumination of a sample is carried out, comprising a first detecting of luminescing sample points, spatially offsetting of the illumination distribution on the sample, a second detecting of luminescing sample points, and determining and storing the position of the detected sample points on a compiled sample image from the values of the spatial offset.

15. An arrangement for collimated microscopic imaging comprising at least two light sources for respectively at least a first illumination and second illumination of a sample, means for generating a patterned light distribution on said sample, at least one detector which is spatially resolving in at least one direction and has a plurality of detector elements, wherein fluorescence is excited by a spatially structured light distribution in partial regions of said sample which are separated from one another, and wherein said partial regions are imaged on the detector in such a way that a definitive association of partial regions and detector elements is carried out; and wherein the spatially structured second illumination is split, wherein one part generates a line-shaped periodically patterned light distribution in the sample, and another part forms double lines which limit the periodic light distribution axially and/or laterally.

16. The arrangement according to claim 15, wherein said pattern is moved by moving a beam-deflecting element in the illumination beam path and/or the sample is moved by a scanning table, and wherein a detection of the fluorescent light emitted by the sample is carried out so as to be synchronized with said movement.

17. The arrangement according to claim 15, wherein a spatially structured second illumination is superimposed with an unpatterned first illumination in the sample.

18. The arrangement according to claim 15, wherein said association of partial regions and detector elements can be adjusted by means of an optical zoom and by tilting a transparent, plane-parallel plate inserted in the illumination beam path and/or detection beam path.

19. The arrangement according to claim 15, wherein said first and second illumination is line-shaped.

20. The arrangement according to claim 15, wherein a pupil of the illumination beam path of said first and second illumination is completely filled in one spatial direction.

21. The arrangement according to claim 15, further comprising phase masks in an illumination beam path of said first and second illumination for generating limiting double lines, which phase masks have a phase jump in their center and/or in a symmetrical edge area.

22. The arrangement according to claim 15, further comprising an optical grating for at least partial splitting of partial beams of the second illumination, wherein the splitting is carried out by the zeroth and +/− first diffraction order of the grating.

23. The arrangement according to claim 22, wherein said optical grating is designed so as to be variable perpendicular to a structuring direction in frequency and/or in the magnitude of a phase jump so that the direction and/or the intensity of the diffraction orders can be adjusted by translation of the grating.

24. The arrangement according to claim 21, wherein said phase masks are arranged after the zeroth diffraction order of the grating.

25. The arrangement according to claim 21, wherein said phase masks have a phase jump in their center or in a symmetrical edge area.

26. The arrangement according to claim 21, wherein said phase masks are designed so as to be variable in position and/or in the magnitude of the phase jump in a direction perpendicular to a line-shaped illumination so that different characteristics of the influencing of the light can be adjusted by translation of the phase masks.

27. The arrangement according to claim 15, wherein axially and laterally limiting double lines and periodically patterned light distribution overlap one another incoherently in the sample.

28. The arrangement according to claim 15, wherein incoherence of the overlapping is affected by polarization orthogonal to one another or by different wavelengths or by a retardation of overlapping partial beams.

29. The arrangement according to claim 15, wherein the spatially resolving detector is a row detector in front of which is arranged a variable slit diaphragm.

30. The arrangement according to claim 15, wherein an illumination is provided in parallel with a plurality of lines and detection by a spatially resolving, planar detector.

* * * * *

UNITED STATES PATENT AND TRADEMARK OFFICE
CERTIFICATE OF CORRECTION

PATENT NO.        : 8,207,510 B2
APPLICATION NO.   : 13/042137
DATED             : June 26, 2012
INVENTOR(S)       : Michael Kempe et al.

It is certified that error appears in the above-identified patent and that said Letters Patent is hereby corrected as shown below:

In the Specification

Column 8, line 47, now reads: "to the switching off of the Dropna molecules …"
should read -- o the switching off of the Dronpa molecules … --.

Signed and Sealed this
First Day of April, 2014

Michelle K. Lee
*Deputy Director of the United States Patent and Trademark Office*